United States Patent [19]

Kleinerman

[11] 4,146,604

[45] Mar. 27, 1979

[54] DIFFERENTIAL COUNTING OF LEUKOCYTES AND OTHER CELLS

[75] Inventor: Marcos Y. Kleinerman, Webster, Mass.

[73] Assignee: Block Engineering, Inc., Cambridge, Mass.

[21] Appl. No.: 438,162

[22] Filed: Jan. 30, 1974

Related U.S. Application Data

[63] Continuation-in-part of Ser. No. 365,460, May 31, 1973, Pat. No. 3,916,205.

[51] Int. Cl.² ..................... G01N 21/38; G01N 33/16
[52] U.S. Cl. .......................................... 424/3; 8/1 W;
  8/3; 23/230 B; 250/302; 252/301.16; 252/408;
  424/7; 424/8
[58] Field of Search ............... 252/301.2 R, 301.2 W,
  252/301.2 P, 408, 301.16; 424/3, 7, 8; 8/1 W, 3;
  250/302

[56] References Cited

U.S. PATENT DOCUMENTS 3,386,920  6/1968  Alburger ............................ 252/301.2
3,586,859  6/1971  Katz ........................................ 424/7

OTHER PUBLICATIONS

Chem. Abs., vol. 77, 1972, No. 111142g.
Chem. Abs., vol. 78, 1973, No. 13514f.
Pearse, Histochem., Little, Brown & Co., Boston, 1960, pp. 731–733.

*Primary Examiner*—Anna P. Fagelson
*Attorney, Agent, or Firm*—Schiller & Pandiscio

[57] ABSTRACT

A novel composition of matter, process and apparatus is provided for distinguishing and absolutely counting leukocytes, erythrocytes, reticulocytes, and other cells as well as differently counting and classifying the different types of leukocytes. The composition of matter comprises a plurality of compatible dyes for uniquely distinguishing leukocytes, erythrocytes, reticulocytes, and other cells randomly distributed in a medium. At least one of the dyes imparts a characteristic fluorescence to all leukocytes stained therewith. The nature of the dye composition is such that when the stained leukocytes are irradiated with radiation having the characteristic absorption wavelengths of each dye, the relative intensities of the light emitted and/or transmitted by each leukocyte type defines that particular leukocyte type. Apparatus is therefore provided for irradiating the medium with the characteristic radiation and measuring the radiation emitted by the irradiated leukocytes in each of their characteristic wavelength regions.

25 Claims, 3 Drawing Figures

FIG. 3

DIFFERENTIAL COUNTING OF LEUKOCYTES AND OTHER CELLS

This application is a continuation-in-part of my copending U.S. application Ser. No. 365,460 filed May 31, 1973 now U.S. Pat. No. 3,916,205 entitled Differential Counting of Leukocytes and Other Cells.

The present invention relates to improvements in bioanalytical staining techniques, and more particularly to a method of staining biological samples with fluorescent dyes.

The present techniques of microscopic study of the structure or morphology of a biological sample are severely restricted by the spatial resolving power of the optical instrument used. One common technique involves the use of a plurality of dyes, each dye being specific for a particular constituent or micro-structure to be differentiated. After dyeing, the various aspects of the structure can be distinguished, from one another by the color contrast. Because this method requires ratioing, it is clearly affected by resolution limitations as well as other factors which may effect the maintainance of spatial coherence.

Also, present methods, for determining the correlation of the spatial distribution of two or more microstructures or constituents, are limited by the resolving power of the optical measuring device being used.

For many purposes, it is not necessary to determine the exact shape and size of the microstructure; an indication of its existence may be sufficient. In such cases, one need only determine the coexistence of the several constituents defining the structure being assayed, there being a number of reagent reactions used for just this purpose. However, most of such reagent reactions are destructive of the sample or are of such other nature as to preclude making additional measurements on the same sample.

A number of other problems exist in the use of analytical staining techniques for micro assay of biological samples. One common problem is the detection of small changes in signal intensity of characteristic light due to the stain, in the presence of a large background intensity. This problem has been partially solved by the use of fluorescent staining, a well known and useful process. Locating a dye with the desired specificity for a particular microstructure or constituent is considered a serious problem in the development of new staining techniques; the problem is further aggrevated when one wished to use fluorescent dyes or stains, since the number of such available stains is quite small, for example, being considerably smaller than the number of known non-fluorescent biological stains. The term "fluorescent stain" is intended to include fluorochrome as well as fluorescent stains or dyes, where the context so permits.

Another problem encountered in biological staining techniques is due to low dye loading, i.e. poor dye takeup by the microstructure in question. In the case of fluorescent and fluorochrome staining, low dye loading leads to low signal strengths even for reasonable levels of the energy of excitation. Such low levels of signal, together with the typically small size of many samples, greatly restricts the usefulness of fluorochrome staining techniques because of the difficulties in detecting the signal. The present approach to solving this problem is to increase the irradiance of the excitation energy or to attempt to increase the dye loading. Such approach is only partially successful because there is usually a limit to the amount of dye which can be attached to a given structure, and the level of possible irradiation is limited either by the lack of an adequate source or the distinct possibility of damaging or destroying the sample by overly large radiation dosage.

Further, even if the dye loading can be increased, the signal emitted by a fluorochrome stain may not increase linearly with dye loadings at high concentrations, because self-quenching usually occurs.

Another problem often encountered in biological staining processes is photochemical bleaching of the stain. While this problem is most often encountered at high illumination levels, it is nevertheless important. The present tendency toward use of high powered illumination sources such as lasers, makes the bleaching characteristics of the dyes quite important.

It should be noted that the relatively broad spectral signature of stains limited to the relatively narrow spectral region in which such stains emit or absorb strongly limits the number of channels of information which can simultaneously be obtained from a given sample. This particular problem should not be confused with the possible number of combinations of stains which is limited by the chemical compatibility of their properties. The problem of the spectral response of the dyes is more acute in the case of fluorochrome stains, each of which requires, in effect an emission channel and an adsorption channel in the optical equipment used.

With reference to a particular use of biological staining techniques, there are several methods and systems for counting and classifying leukocytes. In the usual method, a cytotechnician microscopically views a blood smear prepared on an ordinary microscope slide that has been stained with one of the Romanowsky stains, such as the Wright or Giemsa stains. The cytotechnician sequentially examines 100 leukocytes and classifies each accordingly to its type. Not only is this method time consuming, but it suffers also from the disadvantage of limited reliability relative to counting and classifying of the less abundant cells such as monocytes, eosinophils and basophils. In a recently developed automated system, the leukocytes are made to flow through three or four different channels, each channel provided with means for staining the leukocytes flowing therein with a particular dye. Due to the fact that several channels and different chemical treatments are required for each cell type, such a system suffers from the disadvantages that it is complex in design and costly to manufacture. In another automatic system, a selected region of a blood smear, stained in the usual manner with a Romanowsky stain, is scanned mechanically under a microscope provided with an electronic image tube. When a leukocyte is in the field of view of the image tube, the slide is stopped. An image analyzing computer connected to the image tube classifies the leukocyte according to its cell profile and cytoplasm color. Since this system requires the services of a technician to select a region of the smear suitable for automatic scanning, such systems have suffered from the disadvantages of being time consuming and costly.

It is therefore the primary purpose of the invention to provide a method of staining of biological structures, which method overcomes, in whole or in part, many of the above mentioned problems.

Yet another object of the present invention is to provide a method for generating a comparatively large signal from a fluorochrome dye with low dye loadings and reasonable levels of excitation irradiation. Another object of the present invention is to provide a biological staining technique whereby one may determine the existence of a plurality of structures using a single signal rather than a pair of spatially related signals, and without requiring a chemical reaction. Yet another object of the present invention is to provide a technique which yields the correlation in the spatial distribution of a plurality of substances in a microstructure, with a spatial resolution better than the limits imposed by the particular optical technique employed.

Yet another object of the present invention is to provide a composition of matter, a method and an apparatus involving the automatic absolute counting of leukocytes, erythrocytes reticulocytes, and other cells, and the differential counting and classifying of leukocyte types which do not suffer from the heretofore mentioned disadvantages. To this latter end, the present invention provides a dye composition for distinguishing eosinophils, monocytes, lymphocytes, mature and immature neutrophils, erythrocytes and reticulocytes randomly distributed in a blood medium. The dye composition comprises a plurality of compatible dyes, at least one of the dyes imparting a characteristic fluorescence to all leukocytes stained therewith. The dye composition is such that, when the stained leukocytes are irradiated with optical radiation having the characteristic absorption wavelengths of each dye, the relative intensities of the light emitted and/or transmitted by each leukocyte type defines a particular leukocyte type.

To effect the foregoing and other objects of the present invention, the present technique makes use of the intermolecular transfer of energy between a sensitizer and a fluorescent dye which is in sufficiently close proximity to the sensitizer so that some of the energy absorbed by the latter is made available to excite fluorescence in the fluorescent dye.

It is important to note that the transfer mechanism of interest here is intermolecular, it being believed that the energy is transferred by a resonance phenomenon. Consequently, the sensitizer and the emitter dye need not combine to form a compound in order for the energy transfer to take place. All that is required is that the sensitizer and fluorescent dye have some similar excitation levels which are within about a few hundred Angstroms of each other. This permits the sensitizer-dye combination to work as a mixture, rather than as a compound.

The term "fluorescence" is intended to mean a luminescence stimulated by radiation and emitted during stimulation. In the mixtures used in one aspect of the present invention, the fluorescence is sensitized, i.e. luminescence is stimulated in one component when the mixture is irradiated or illuminated by radiation which is primarily absorbed by the other component. It should be noted that the luminescence from a sensitized mixture may consist of radiation from more than one of the elements of the mixture. Basically, the mechanism of sensitized fluorescence involves the absorption of radiation by one component of the mixture (referred to here as the sensitizer) to produce excited molecules. The excited molecules of the sensitizer, being in close proximity to those of the sensitized dye or emitter, transfer energy to molecules of the latter, exciting them into emission. The energy transfer as previously noted is believed to be through a resonance process, a singlet-signlet energy transfer dependent on the distance between donor and acceptor.

Three cases of interest may be distinguished with respect to the disposition of the sensitizer and the emitter within the microstructure being assayed:

(1) The sensitizer can be distributed more or less uniformly throughout the microstructure while the emitter is used to stain preferentially a specific microstructure or constituent;

(2) The sensitizer is distributed selectively within the sample, i.e. preferentially with respect to a specific microstructure or constituent while the emitter is uniformly distributed; and (3) Both the stain and the sensitizer are preferentially distributed with respect to different constituents or microstructure.

This last case provides a substantial advantage over current staining techniques wherein dye sensitization by an appropriate absorption is achieved only on a molecular level because then the sensitizer and stain must be specific to the same material.

The sensitizer is intended in effect to act as a radiation collector for the emitting dye or stain. In the simplest case, the maximum energy available for fluorescence is the sum of that transferred from the sensitizer and that absorbed directly by the dye itself. The energy transferred from the sensitizer is dependent upon the quantity and disposition of the latter while of course the energy absorbed by the dye depends on the quantity and disposition of the dye itself. To achieve high emission from a small volume of a low concentration dye, one need only provide a sufficient quantity of the sensitizer by loading it at an appropriate concentration.

The sensitizer itself can be a stain or may be non-staining. Where fluorescence from a sensitizer cannot readily be observed, one can still obtain a fluorescent signal by mixing the sensitizer with an appropriate emitter. This would permit one to observe weak absorption signals more reliably as small emission signals on a dark background rather than as small signals on a bright background. This also permits the synthesis of fluorescent signals from dyes which may not provide observable fluorescence in a particular absorbing medium which thereby increases the choice of fluorescent stains of desired specificity. The current art, on the other hand, requires combining the constituents of the dye chemically to form a fluorescent compound.

It can now be seen how the use of intermolecular energy transfer permits the performance of correlations of the spatial distribution of two substances. For example, a sensitizer-emitter combination is chosen so that the sensitizer attaches to one of the two substances and the emitter attached to the other. If the substance is now illuminated in the absorption band of the sensitizer and observed in the emission band of the emitter the observed signal is a measure of the correlation of the spatial distribution of the two substances.

Since the energy transfer mechanism appears to depend upon resonance, the spatial resolution which can be observed by the method of the present invention is in the order of a few tens of Angstroms. This resolution corresponds to the proximity which must occur between the sensitizer and emitter, and is independent of the optical resolution of the observing system.

Bleaching of the dye due to multiple photon saturation may be reduced by using a sensitizer in combination with the emitter. The energy transfer mechanism is critically dependent upon the population of the excited level of the emittting dye, more so than in the case of self-absorption. This serves to limit the transfer as saturation is approached.

One can also use a pair of fluorescent stains in combination as a sensitizer-emitter mixture. Such a combination allows one to measure the concentration of each dye and the correlation of their spatial concentrations, without increasing the number of channels required for observation. In other words, one can obtain n substantially independent measurements from n−1 dyes, i.e. pick up another degree of freedom of measurement.

The term "differential staining" is used herein to mean that the dye being used will stain a given component of the cell type of interest (for instance the protein of said cell type) to a much greater extent than other components (for instance nucleic acids) of the same cell type.

In using a staining mixture of the present invention in classifying leukocytes in a slide scanning method, a drop of blood is spread on a microscope slide and, after fixation, is stained by immersion in the dye composition. In the flow tube method, a small amount of a blood sample, suitably diluted, is stained in a liquid solution of the dye composition and the cells are forced to flow in single file through a capillary tube. In both methods, the stained leukocytes are irradiated under ultraviolet and violet light and their fluorescence is detected through a blue-green filter. The leukocytes are presented with a fluorescence in decreasing order to intensity from eosiniphils to immature neutrophils to mature neutrophils to monocytes to lymphocytes. The stained leukocytes are then irradiated under a green light and the nuclei of the different leukocyte types are detected through a red filter. Leukocytes exhibit a red fluorescence of comparable intensity, reticulocytes fluoresce with an appreciably smaller intensity and normal erythrocytes have a negligible fluorescence. The leukocytes are counted and classified, for example, by measuring the ratio of the blue-green component of cell fluorescence to the red nuclear fluorescence. In the flow tube method, excitation with ultraviolet light produces a strong orange-red component, most pronounced in neutrophils and eosinophils, the intensity of which, with respect to the blue-green component, provides another parameter for distinguishing particular leukocyte types. In addition, the transmitted violet light is measured to distinguish erythrocytes from leukocytes. In contrast to the negligible absorption of violet light by leukocytes, erythrocytes and reticulocytes exhibit an appreciable absorption of violet light.

The invention accordingly comprises the composition, method, steps and apparatus possessing the construction, combination of elements, and arrangement of parts that are exemplified in the following detailed disclosure, the scope of which will be indicated in the appended claims.

For a fuller understanding of the nature and objects of the present invention, reference should be had to the following detailed description taken in connection with the accompanying drawings wherein.

Generally, the invention is carried out by preparing a biological specimen, for example, a blood smear, on a standard microscope slide, allowing it to be fixed by drying or by immersion in alcohol, and then applying the dye and sensitizer to the specimen. The specimen thus prepared is then irradiated with illumination to excite fluorescence and the fluorescent properties of the specimen then examined under a microscope or by some other appropriate optical or electro-optical system well known in the art.

For example, one process embodying the present invention involves the staining of a blood medium with a dye composition comprising a plurality of dyes, at least one of the dyes imparting a characteristic fluorescence to all leukocytes. The dye composition is such that, when the stained blood medium is illuminated with light having the characteristic absorption wavelengths of each dye, the relative intensities of the light emitted and/or transmitted by each cell type at the optical wavelength region of emission and absorption characteristic of each dye uniquely depends, in at least one characteristic wavelength region, on the type of leukocyte. The light emitted by the irradiated leukocytes in each of their characteristic wavelength regions is measured and the leukocyte types are classified according to the relative intensities of the emitted light in the characteristic wavelength region of each dye.

Figure 3:
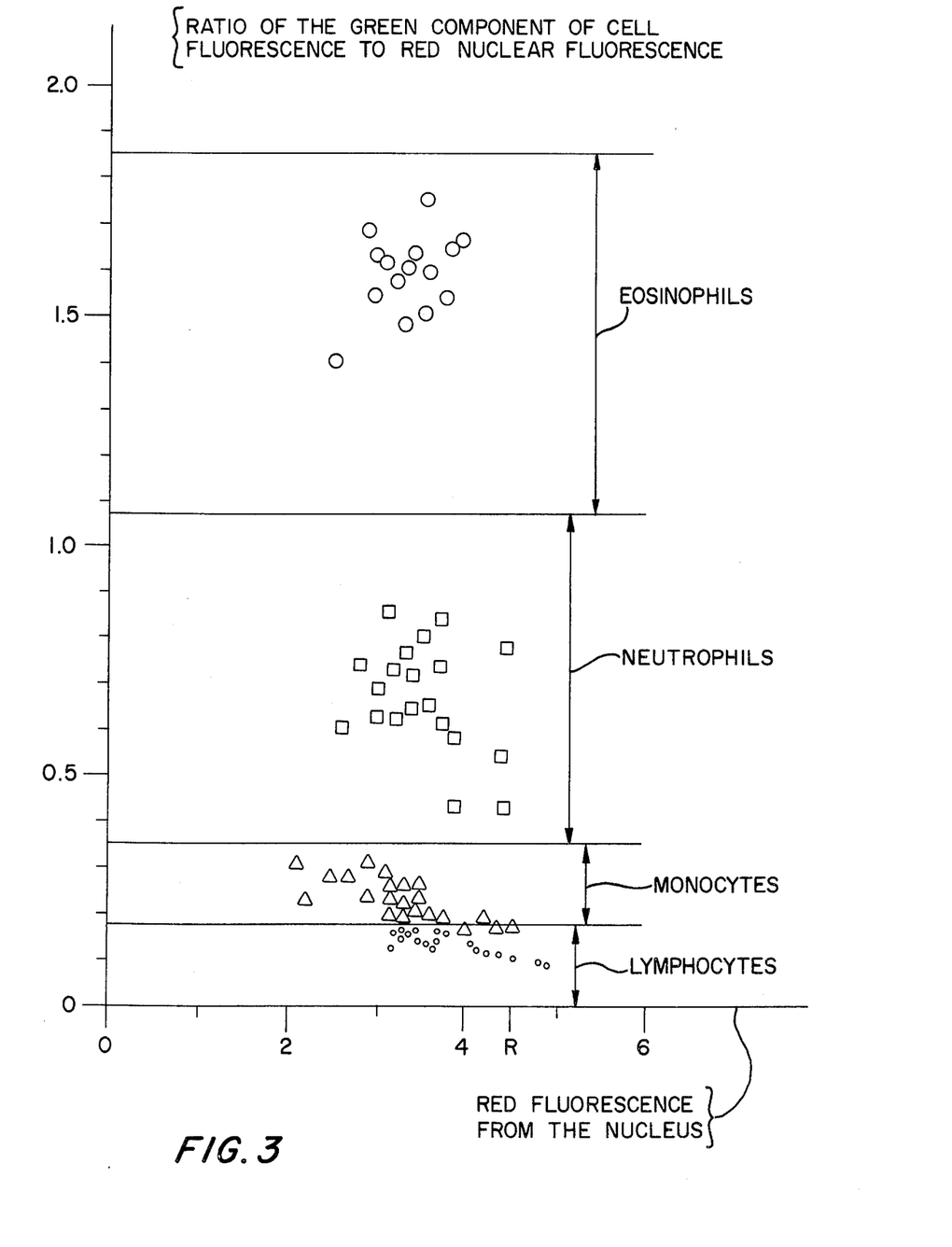
FIG. 3 is a graphic representation illustrating the fluorescent characteristics of selected leukocyte types on a methanol fixed smear stained with one of the mixtures herein described.

In particular, one process embodying the present invention involves the staining of leukocytes randomly distributed in a medium with a dye composition comprising a mixture of (1) a sulfonated triazinyl stilbene derivative, (2) a naphthalene sulfonic acid; and (3) a cationic dye. The stained leukocytes are irradiated with ultraviolet and violet light and detected through a green or blue-green filter. The green component of leukocyte fluorescence is presented with a characteristic fluorescent intensity against a dark background. The stained leukocytes are also irradiated with green light and the red fluorescence of only the nuclei of the cells are detected through a red or orange-red filter. As shown in FIG. 3, the detected leukocytes are characterized by a fluorescence in decreasing order of intensity from eosinophils to neutrophils to monocytes to lymphocytes, each leukocyte type uniquely defined by the ratio of the blue-green component of cell fluorescence to the red nuclear fluorescence with respect to the red fluorescence from the nucleus.

As will be seen from the following examples, the nature of the sensitizer is extremely variable. The sensitizer should be selected to have a large absorption coefficient with respect to incident radiation so that an ample amount of energy is thereby available to be transferred to the dye. Further, the sensitizer should have a relatively long life time in its excited state so as to give an ample opportunity for the energy transfer to occur between the sensitizer and dye. The sensitizer should not be a material which will be sterically impeded from being proximate to a dye molecule. Very importantly, the sensitizer should exhibit a large electrical dipole effect with respect to its transition to an excited state, i.e. it must be a good antenna or radiator which will couple well to the electrons of the dye molecule. This coupling between adjacent molecules is believed not to extend significantly beyond about 30 Å and is usually quite good within 10 Å.

Among the fluorescent dyes which are useful in the present invention are those which preferentially dye protein, such as the cytoplasm of white blood cells and granules in granulocytes, particularly dyes such as sulfonated triazinyl derivatives or a diamino stilbene having each amino group in each of the phenyl rings of the stilbene molecule, and their alkyl, alkoxy or halogen substituted derivatives, for example 4,4'-bis (4-(3 sulfoanilino)-6(bis (2-hydroxy-ethyl)-amino) -1,3,5, triazin-2yl) amino stilbene 2,2'-disulfonic acid tetrasodium salt (hereinafter referred to as LN). For these dyes, the optimum excitation wavelength band is in the range of 320 to 390 mμ and the optimum fluorescent wavelength band is 440 to 550 mμ. These dyes impart a strong blue fluorescence to the protein of leukocytes and the neutrophil grannules and a weaker blue fluorescence to eosinophils, monocytes and lymphocytes.

The structure of LN is believed to be as follows:

Fluorescent dyes suitable for specifically dyeing eosinophil granules are the anilino or toluidino naphthalene sulfonic acids and their alkyl, alkoxy or halogen substituted derivatives; 4,4' diamino stilbene 2,2' disulfonic acid, N, N, N', N' tetraacetic acid and its alkyl, alkoxy or halogen substituted derivatives; sulfonated fluorescent derivatives of 1,8 naphthalimide, such as brilliant sulfaflavine (hereinafter called BSF) and its alkyl, alkoxy or halogen substituted derivatives; 8-p-toluidino-1 naphthalene sulfonic acid and its alkyl, alkoxy or halogen substituted derivatives; and 8-hydroxy-1,3,6 pyrene trisulfonic acid and its alkyl, alkoxy and halogen derivatives. The anilino and toluidino naphthalene sulfonic acids have an optimum exciation wavelength band in the range of 320 to 410 mμ and an optimum fluorescent wavelength band in the range of 440 to 550 mμ. Brilliant sulfaflavine has an optimum excitation wavelength band in the range of 360 to 450 mμ and an optimum fluorescent wavelength band in the range of 480 to 550 mμ. These dyes strongly stain the eosinophil granules with a green-blue or green fluorescence.

Dyes which impart a strong red fluorescence to the nucleic acids of leukocytes, mainly in the nuclei, preferably are cationic dyes, for example the phenanthridinium dyes such as an ethidium halide, (2,7 diamino - 10 ethyl-9 phenyl phenanthridinium bromide, hereinafter referred to as EB) and its alkyl, alkoxy or haolgen derivatives; and in dry smears, acridine orange; and rhoduline orange. Ethidium bromide has an optimum excitation wavelength range of 480 to 550 mμ and an optimum fluorescent wavelength range of 580 to 650 mμ. The structure of EB is believed to be as follows:

A large number of other fluorescent dyes can be used, such as many of those described in *Biological Stains*, R. D. Lillie, The Williams & Wilkins Co., Baltimore, 1969.

The sensitizer material should be chemically compatible with the fluorescent emitting stain, i.e. it should not form chemical compounds with the dye by covalent or dative bonding which would destroy or reduce the original optical properties or chemical affinities of the dye and sensitizer. The sensitizer should be bound (as by Van der Waals forces, chemical bonds, etc.) to some cell constituent in a manner so that it is proximate or accessible to the dye, or should be dissolved in some cell constituent.

Obviously, if the sensitizer is also a fluorescent dye, it should be selected to that its emission bands are readily distinguishable from those of the emitting dye.

Figures 1, 2:
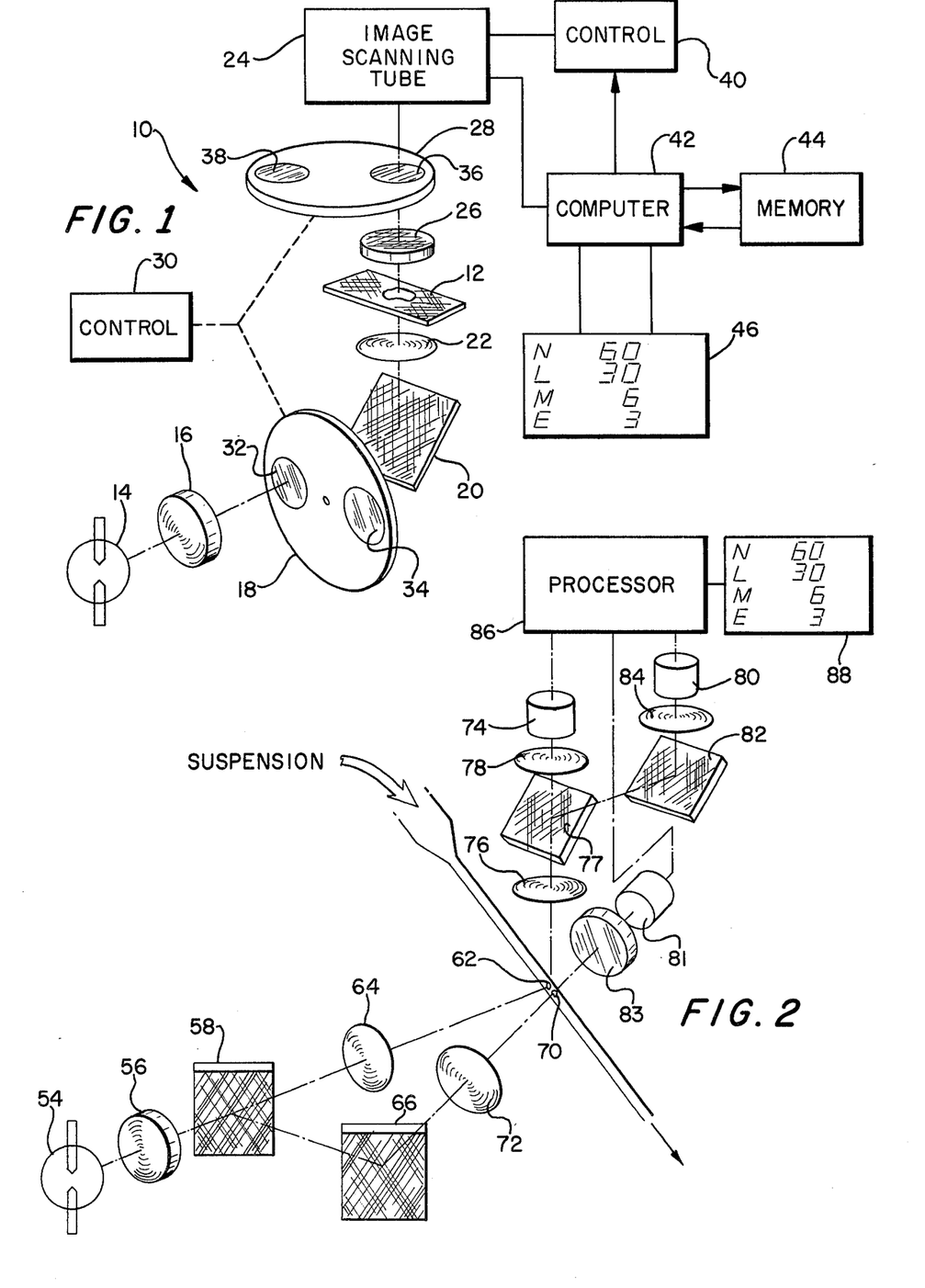
FIG. 1 is a block and schematic diagram of a slide scanning system for differential counting of leukocytes.
FIG. 2 is a block and schematic diagram of a flow tube system for differential counting of leukocytes.

Referring now to FIG. 1, there is shown a slide scanning system 10 for differentially counting leukocytes. By way of example, an alcohol-fixed blood smear 11 on a slide 12 is immersed in a preferred dye solution comprising $1 \times 10^{-4}$ molar ethidium bromide; $1 \times 10^{-3}$ to $1 \times 10^{-4}$ molar brilliant sulfaflavine; and $1 \times 10^{-4}$ molar 4,4' bis [4-(3-sulfoanilino)-6[bis (2-hydroxy-ethyl)amino]-1,3,5, triazin-2yl] amino stilbene 2,2' disulfonic acid tetrasodium salt in a solvent including a buffer of 0.01 to 0.1 molar 2-amino-2 (hydroxymethyl) -1,3 propanediol-HCl, commonly known as tris-HCl, at a pH concentration range of 8.0 to 10.0, for best results, the pH concentration range is 8.5 to 9.5. In alternative embodiments, the buffer is other than tris-HCl, for example sodium borate or sodium bicarbonate. After a staining time of approximately 10 minutes, slide 12 is rinsed in an aqueous solution, for example distilled water, for approximately 1 minute and then dried.

Thereafter slide 12 is irradiated with illumination from a source 14, for example a mercury arc lamp, which is focused thereon via a collimating lens 16, an excitation filter wheel 18, a beam splitter 20 and a condensing lens 22. Filter wheel 18 includes a filter 32 which transmits ultraviolet and violet light, for example 320 to 440 nanometers and a filter 34 which transmits green light, for example the 546 nanometer mercury band. In the illustrated embodiment, by way of example, beam splitter 20 is a dichroic mirror. In alternative embodiments, beam splitter 20 is other than a dichroic mirror, for example a reflector such as a straight surface mirror. The field of view containing the fluorochromed leukocytes is imaged on a photoelectronic device 24, for example the photosensitive surface of an image scanning tube, via a collimating lens 26 and an emission filter wheel 28. Filter wheel 28 includes a blue-green filter 36 and a red filter 38. As hereinafter described, filter wheels 18 and 28 are indexed by means of a controller 30.

Initially, controller 30 indexes filter wheels 18 and 28 in such a manner that filters 32 and 36 are positioned in the transmitted light path. That is, slide 12 is irradiated with ultraviolet and violet light and blue-green fluorescent images are presented at the photosensitive surface of image scanning tube 24 via blue-green filter 36. The green components of leukocyte fluorescence appear against a dark background with a fluorescence in decreasing order of intensity from eosiniphils to neutrophils to monocytes to lymphocytes. Increasing the excitation radiation from 360 to 440 nanometers with respect to that from 320 to 360 nanometers, maximizes the difference between the fluorescent intensities of the eosiniphils and neutrophils. The photosensitive surface of image tube 24 is scanned in a specified pattern determined by a control 40 which is programmed by a computer 42. The intensity of the irradiated leukocytes are measured by computer 42 and data signals for each measurement are stored in a memory 44 at X,Y address location corresponding to the X,Y positions on the photosensitive surface of image scanning tube 24.

Controller 30 then indexes filter wheels 18 and 28 in such a manner that filters 34 and 38 are positioned in the transmitted light path. That is, slide 12 is irradiated with green light and red fluorescent images are presented at the photosensitive surface of image scanning tube 24 through red filter 38. In this case, only the red fluorescence of the nuclei of the leukocytes appear against a dark background at the photosensitive surface of image tube 24. In the manner hereinbefore described, the fluorescent intensities of the nuclei at each of the X,Y positions on the photosensitive surface of image scanning tube 24 are measured by computer 42. The measurement data stored in memory 44, i.e., the green component of cell fluorescence, is addressed into computer 42 for determining leukocyte types by generating differential counting data signals representing the ratio of the green component of cell fluorescence to red nuclear fluorescence with respect to the red fluorescence from the nucleus as shown in FIG. 3. Cell profile data signals, i.e. a measurement of the time period during which a signal from a cell is received, distinguish lymphocytes from monocytes. The differential counting data signals generated by computer 42 are applied to a display 46, for example a digital display of the relative abundance of the different cell types, for visual presentation. It is to be understood that, in alternative embodiments display 46 is other than a digital display, for example a cathode-ray tube, a chart recorder, or a magnetic tape recorder.

It will be readily appreciated that systems other than that shown in FIG. 1 can be used for differentially counting and classifying leukocytes types on a stained blood smear. For example, a manual system wherein the stained slide is irradiated in the manner hereinbefore described and observed through a microscope. In alternative embodiments, the irradiated leukocytes are detected by means other than an image scanning tube, for example one or a plurality of photo-detectors and a flying spot scanner.

Referring now to FIG. 2, there is shown a flow tube system 50 for differential counting of leukocyte types. By way of example, a blood sample is diluted in a saline solution and the cells are fixed with formaldehyde. It is to be noted that the cells can be fixed with formaldehyde prior to or after dilution. The white cells are stained in a solution comprising $1 \times 10^{-4}$ molar 4,4' bis [4-(3 sulfoanilino)-6-[bis (2-hydroxy ethyl) amino]-1,3,5 triazin-2yl]amino stilbene; $1 \times 10^{-3}$ to $1 \times 10^{-4}$ molar brilliant sulfaflavine; and $1 \times 10^{-4}$ molar ethidium bromide. The resulting suspension is diluted and buffered with either 0.1 molar tris-HCl or 0.05 molar borax at a pH in the range of 9.0 to 9.2. As an example, the blood sample has a dilution range of fifty to one hundred fold in the suspension, the final concentration of which is approximately $1 \times 10^{-4}$ molar or less in each of the fluorescent dyes. The cells are made to flow single file through a narrow tube 52, for example a capillary tube, wherein each of the leukocytes is irradiated with illumination from a source 54, for example a mercury arc lamp. The illumination generated by mercury arc lamp 54 is directed through a collimating lens 56 to a reflecting filter 58, for example a dichroic filter. The wavelength band of light passing through dichroic filter 58 is focused on capillary tube 52 at 62 via a condensing lens 64. In the illustrated embodiment, by way of example, dichroic filter 58 transmits green light in the 546 nanometer mercury band. The wavelength band of light reflected by dichroic filter 58 is directed to a reflecting filter 66, for example a dichroic filter and focused on capillary tube 52 at 70 via a condensing lens 72. In the illustrated embodiment, by way of example, dichroic filter 66 reflects ultraviolet and violet light in the 320 to 410 nanometer mercury band. It is preferred that the distance between the locations denoted by reference characters 62 and 70 is typically in the range of 50 to 200 microns. A photo-electric device 74, for example a photo-multiplier senses the blue-green emission light from capillary tube 52 via a collecting lens 76, a dichroic mirror 77 and a blue-green emission filter 78. A photo-electric device 80, for example a photo-multiplier, senses the orange-red emission light from capillary tube 52 via collecting lens 76, dichroic mirror 77, a dichroic mirror 82 and an orange-red emission filter 84. A photo-electric device 81, for example a photodiode, senses the ultraviolet and violet light at 70 via an emission filter 82 having a pass band in the approximate range of 410 to 430 nanometers.

Photo-multiplier 74 detects the blue-green component of cell fluorescence, and photo-multiplier 80 detects the red nuclear fluorescence, and photo-multiplier 81 detects violet light. Erythrocytes and reticulocytes are characterized by appreciable absorption of violet light and leukocytes are characterized by negligible absorption of violet light. Accordingly, photo-multiplier 81 detects the violet light absorption for distinguishing red cells from white cells.

Data signals generated by photo-multipliers 74 and 80 are applied to a processor 86, for example a small dedicated computer, wherein the detected leukocyte fluorescences are differentially counted and classified as the ratio of the green component of cell fluorescence to the red nuclear fluorescence with respect to the red fluorescence from the nucleus for each leukocyte type. Differential counting data signals generated by computer 86 for each leukocyte passing through capillary tube 52 are applied to a display 88, for example a digital display of the relative abundance of the different cell types, for presentation. In addition, data signals generated by photodiode 81, representing a measurement of the absorbed violet light, are applied to computer 86 for distinguishing erythrocyte and leukocytes. Leukocyte types can be distinguished from one another by measuring light scattered by the leukocytes by means of photodetectors, for example photodiodes. It is to be understood that, in alternative embodiments, display 88 is other than a digital display for example, a cathode-ray tube, a chart recorder or a magnetic tape recorder. Furthermore, it is to be understood that, in alternative embodiments, the light emitted from source 54 is directed to tube 52 by means other than a pair of beam splitters, for example, two sources each emitting light which is directed towards tube 52 or a source characterized by a scanning light beam.

The following examples are illustrative of the principles of the present invention and, for the sake of simplicity, all are limited to blood as the biological specimens.

EXAMPLE I

A drop of whole blood is placed on a microscope slide and spread into a thin film with the aid of another microscope slide. After the film has dried, the blood smear is fixed by immersing the slide in methyl alcohol for five minutes. Thereafter, the slide is immersed in a liquid mixture comprising:

1. 100 parts per million of 4,4'-bis [4-(3 sulfoanilino)-6-[bis (2-hydroxy-ethyl)-amino]-1,3,5 triazin-2yl] amino stilbene 2,2'-disulfonic acid tetrasodium salt, (LN);
2. 1,000 parts per million of brilliant sulfaflavine;
3. 30 parts per million of ethidium bromide (EB) which is sensitized by the LN; and
4. a solvent comprising 12,000 parts per million of 2-amino-2(hydroxymethyl)-1,3 propanediol and enough concentrated hydrochloric acid solution to bring the pH of the solution to 9.0.

After ten minutes in the liquid mixture, the slide is rinsed in distilled water for one minute and then dried.

EXAMPLE II

One part of whole blood is mixed with four parts of a solution at a pH of 9.0 comprising:

1. 1,200 parts per million of 2-amino-2(hydroxymethyl)-1,3 propanediol-HCl buffer pH 9.0;
2. 85,000 parts per million of sodium chloride;
3. 1,000 parts per million of brilliant sulfaflavine;
4. 100 parts per million of 4,4'-bis [4-(3-sulfoanilino)-6-[bis (2-hydroxy-ethyl)-amino]-1,3,5 triazin-2yl] amino stilbene 2,2'-disulfonic acid tetrasodium salt; and
5. 30 parts per million of ethidium bromide.

After three minutes, the suspension is mixed with one part of a 20% solution of formaldehyde. Five minutes later, the mixture is diluted 15 to 20 times with a solution comprising:

6. 12,000 parts per million of 2-amino-2-(hydroxymethyl)-1,3 propanediol-HCl buffer (pH 9.0);
7. 85,000 parts per million of sodium chloride;
8. 100 parts per million of 4,4'-bis [4-(3-sulfoanilino)-6-[bis (2-hydroxy-ethyl)-amino]-1,3,5 triazin -2yl] amino stilbene 2,2'-disulfonic acid tetrasodium salt; and
9. 15 parts per million of ethidium bromide.

In this example, the stained suspended cells exhibit the following optical properties under ultraviolet illumination of approximately 365 nanometers:

(a) The cytoplasm and granules of the neutrophils exhibit a visible fluorescence with spectral peaks in the blue and orange-red regions. The blue component results from the direct excitation of the triazinyl dye and the red component, most pronounced in the granules, is due to energy transfer from the triazinyl dye to ethidium bromide, the latter being present in the grannules, and elsewhere in the cytoplasm, at concentrations which are too small to be efficiently excited by direct absorption of the ultraviolet light.

(b) The cytoplasm and granules of the eosinophils exhibit a stronger visible fluorescence than the neutrophils with spectral peaks in the blue-green and orange-red regions. The blue-green component results mainly from the excitation of the brilliant sulfaflavine dye and the triazinyl dye, and the red-orange component is due to energy transfer from the triazinyl dye and the brilliant sulfaflavine dye to ethidium bromide; the latter being present in the granules, and elsewhere in the cytoplasm at concentrations too small to be efficiently excited by direct absorption of the ultraviolet light.

(c) The cytoplasm and nucleus of lymphocytes and monocytes exhibit a weaker fluorescence than that of either the neutrophils or eosinophils. This fluorescence is characterized by a spectral distribution having a peak in the blue region and a smaller peak or shoulder in the red region, and fluorescence of the monocytes being smaller than the fluorescence of the lymphocytes.

Under violet illumination of approximately 400 to 440 nanometers, the eosinophils exhibit a strong green fluorescence which is several times stronger than that of the other leukocytes.

Under green illumination, the nuclei, and to a lesser extent the cytoplasm, of all the leukocytes exhibit a red fluorescence; eosinophils having the brightest fluorescent intensity, neutrophils and monocytes having comparable fluorescent intensities of a lesser brilliance, and lymphocytes generally having the lowest fluorescent intensity.

It is to be noted that red cells exhibit a negligible fluorescence under any of the above conditions.

EXAMPLE III

One part of whole blood is mixed with one part of a 10% solution of formaldehyde for five minutes. The suspension is then mixed with four parts of a solution comprising:

1. 1,200 parts per million of 2-amino-2-(hydroxymethyl)-1,3 propanediol-HCl buffer (pH 9.0);
2. 85,000 parts per million of sodium chloride;
3. 300 parts per million of 8-p toluidino-1-naphthalene sulfonic acid;
4. 100 parts per million of 4,4'-bis [4-(3-sulfoanilino)-6-[bis (2-hydroxy-ethyl)-amino]-1,3,5 triazin-2yl] amino stilbene 2,2'-sulfonic acid tetrasodium salt; and
5. 20 parts per million of ethidium bromide.

After five minutes, the mixture is diluted 15 to 20 times with a solution comprising:

6. 12,000 parts per million of 2-amino-2-(hydroxymethyl) -1,3 propanediol-HCl buffer (pH 9.0);
7. 85,000 parts per million of sodium chloride;
8. 60 parts per million of 8 toluidino 1 naphthalene sulfonic acid;
9. 100 parts per million of 4,4'-bis [4-(3-sulfoanilino) -6-[bis(2-hydroxy-ethyl)-amino]-1,3,5 triazin-2yl]amino stilbene 2,2'-disulfonic acid tetrasodium salt; and
10. 15 parts per million of ethidium bromide.

In this example, the stained suspended cells exhibit the following optical properties under ultraviolet illumination of approximately 365 nanometers;

(a) The cytoplasm and granules of the neutrophils exhibit a visible fluorescence with spectral peaks in the blue and orange-red regions. The blue component results from the direct excitation of the triazinyl dye and the red component, most pronounced in the granules, is due to energy transfer from the triazinyl dye to ethidium bromide, the latter being present in the granules, and elsewhere in the cytoplasm, at concentrations which are too small to be efficiently excited by direct absorption of the ultraviolet light.

(b) The cytoplasm and granules of the eosinophils exhibit a stronger visible fluorescence than the neutrophils with spectral peaks in the blue-green and orange-red regions. The blue-green component results mainly from the excitation of 8-p-toluidino-1-naphthalene sulfonic acid and the triazinyl dye, and the red-orange component is due to energy transfer from the triazinyl dye and the 8-p-toluidino-1-naphthalene sulfonic acid to ethidium bromide; the latter being present in the granules, and elsewhere in the cytoplasm at concentrations too small to be effectively excited by direct absorption of the ultraviolet light.

(c) The cytoplasm and nuclei of lymphocytes and monocytes exhibit a weaker fluorescence than that of either the neutrophils or eosinophils. This fluorescence is characterized by a spectral distribution having a peak in the blue region and a smaller peak or shoulder in the red region, the fluorescence of the monocytes being smaller than the fluorescence of the lymphocytes.

Under violet illumination of approximately 400 to 440 nanometers, the eosinophils exhibit a strong green fluorescence which is several times stronger than that of the other leukocytes.

Under green illumination, the nuclei, and to a lesser extent the cytoplasm, of all the leukocytes exhibit a red fluorescence; eosinophils having the brightest fluorescent intensity, neutrophils and monocytes having comparable fluorescent intensities of a lesser brilliance, and lymphocytes generally having the lowest fluorescent intensity.

It is to be noted that red cells exhibit a negligible fluorescence under any of the above conditions.

EXAMPLE IV

A dried blood smear is treated with LN in aqueous solution for sufficient time to dye the proteins in the sample. The slide is then washed in water and dried. A solution of acridine orange base in ethanol is then applied to the dyed sample for sufficient time to dye the lipids in the latter. Acridine orange base is believed to have the following structure:

When the treated sample is irradiated with illumination at about 350 m$\mu$, LN will fluoresce at about 470 m$\mu$. Where the LN has dyed protein in close proximity to lipids, energy transfer from the LN (serving as a sensitizer) to the acridine orange base dissolved in the lipids will cause the acridine orange base to fluoresce at about 540 m$\mu$. This latter emission is then indicative of the presence of lipoprotein, although the actual structure may have dimensions well below the resolution capability of the observational equipment.

In one aspect, the present invention provides a single dye composition comprising three fluorescent dyes for uniquely distinguishing leukocytes, erythrocytes and reticulocytes randomly distributed in a medium and a method and apparatus for absolute counting of leukocytes and reticulocytes and differential counting of leukocytes which have been stained with such a dye composition. When the stained leukocytes are irradiated by light having the characteristic absorption wavelengths of each dye, the relative intensities of leukocyte fluorescence at the optical wavelength region of emission of each dye uniquely depends, in at least one characteristic wavelength region, on the type of leukocyte. The light emitted by the irradiated leukocytes in each of their characteristic wavelength regions is measured and the leukocyte types are classified according to the relative intensities of the emitted light in the characteristic wavelength region of each dye. Transmitted violet light is measured to distinghish erythrocytes, reticulocytes and leukocytes, erythrocytes and reticulocytes exhibiting appreciable absorption of violet light and leukocytes exhibiting negligible absorption of violet light.

Since certain changes may be made in the foregoing disclosure without departing from the scope of the invention herein involved, it is intended that all matter contained in the above description and depicted in the accompanying drawings be construed in an illustrative and not in a limiting sense.

What is claimed is:

1. A mixture for staining a biological cell and comprising, in combination;
   a fluorescent dye capable of dyeing a first specific constituent of said cell, said dye being a sulfonated triazinyl derivative of diamino stilbene, and
   a sensitizer compound capable of being coupled to a different specific constituent of said cell and capable of absorbing incident radiation in a spectral absorption band and of transmitting to dye disposed adjacent to said compound, at least part of the energy of the absorbed incident radiation to excite said dye into fluorescent emission.

2. A dye mixture for distinguishing among biological cell types, said mixture comprising a plurality of compatible dyes, which dyes differentially stain characteristic structures of the cells types of interest, one of said dyes being a sulfonated triazinyl derivative of diamino stilbene, which differentially fluorochrome stains protein structures of the cell types of interest, another one of said dyes being a cationic dye which differentially stains nucleic acids in the cell types of interest.

3. The mixture as defined in claim 2 wherein said cationic dye is a phenanthridium dye.

4. The mixture as defined in claim 3 wherein said phenanthridium dye is ethidium bromide.

5. The mixture as defined in claim 2 wherein said sulfonated triazinyl derivative of diamino stilbene is 4,4' bis[4-(3 sulfoanilino)-6-[bis (2-hydroxy ethyl) amino]-1,3,5 triazin-2yl] amino stilbene 2,2' disulfonic acid tetrasodium salt.

6. The mixture as defined in claim 5 wherein said cationic dye is a phenanthridium dye.

7. The mixture as defined in claim 6 wherein said phenanthridium dye is ethidium bromide.

8. A dye mixture for distinguishing among blood cells, said mixture comprising a plurality of compatible dyes, which dyes differentially stain characteristic structures of the cells types of interest, one of said dyes being a sulfonated triazinyl derivative of diamino stilbene, which differentially fluorochrome stains the cytoplasm of leukocytes and the granules of granulocytes, another one of said dyes being a cationic dye which differentially stains nucleic acids in said blood cells and the filaments network structure of reticulocytes.

9. The mixture as defined in claim 8 wherein said cationic dye is a phenanthridium dye.

10. The mixture as defined in claim 9 wherein said phenanthridium dye is ethidium bromide.

11. The mixture as defined in claim 8 in which another one of said dyes is a sulfonated fluorescent derivative of 1,8 naphthalimide which differentially stains the granules of eosinophils.

12. The mixture as defined in claim 11 wherein said sulfonated fluorescent derivative of 1,8 naphthalimide is brilliant sulfaflavine.

13. The mixture as defined in claim 8 in which another one of said dyes is a toluidino derivative of naphthalene sulfonic acid which differentially stains the granules of eosinophils.

14. The mixture as defined in claim 13 wherein said toluidino derivative of naphthalene sulfonic acid is 8-p-toluidino-1-naphtheline sulfonic acid.

15. A dye mixture for differentially staining biological cells said mixture comprising:
(a) a sulfonated triazinyl derivative of diamino stilbene;
(b) a cationic dye; and
(c) a sulfonated fluorescent derivative of 1,8 naphthalimide.

16. The mixture as defined in claim 15 wherein said sulfonated triazinyl derivative of diamino stilbene is 4,4' bis [4-(3 sulfoanilino)-6-[bis (2-hydroxy-ethyl) amino]1,3,5 triazin-2yl] amino stilbene 2,2' disulfonic acid tetrasodium salt.

17. The mixture as defined in claim 15 wherein said cationic dye is a phenanthridium dye.

18. The mixture as defined in claim 17 wherein said phenanthridium dye is ethidium bromide.

19. The mixture as defined in claim 15 wherein said sulfonated fluorescent derivative of 1,8 naphthalimide is brilliant sulfaflavine.

20. A dye mixture for differentially staining biological cells said mixture comprising:
(a) a sulfonated triazinyl derivative of diamino stilbene;
(b) a cationic dye; and
(c) a toluidino derivative of naphthalene sulfonic acid.

21. The mixture as defined in claim 20 wherein said sulfonated triazinyl derivative of diamino stilbene is 4,4' bis [4-(3 sulfoanilino)-6-[bis (2-hydroxy-ethyl) amino] 1,3,5 triazin-2yl] amino stilbene 2,2' disulfonic acid tetrasodium salt.

22. The mixture as defined in claim 20 wherein said cationic dye is a phenanthridium dye.

23. The mixture as defined in claim 22 wherein said phenanthridium dye is ethidium bromide.

24. The mixture as defined in claim 20 wherein said toluidino derivative of naphthelene sulfonic acid is 8-p-toluidino-1-naphthalene sulfonic acid.

25. A method of staining a biological cell and comprising,
differentially dyeing specific constituents of said cell with a mixture of a fluorescent dye capable of dyeing a first of said constituents, and a sensitizer compound capable of being coupled to a different one of said constituents and capable of absorbing incident radiation in a spectral absorption band and of transmitting to said dye bound to said first constituent adjacent to said sensitizer compound coupled to said different constituent, at least part of the energy of the absorbed incident radiation, thereby to excite said bound dye into fluorescent emission.

* * * * *